United States Patent [19]

Kanemaru et al.

[11] 4,351,971
[45] Sep. 28, 1982

[54] PROCESS FOR PREPARING LOWER ALCOHOLS

[75] Inventors: Kanemaru, Chigasaki; Kenji Yoshida, Fujisawa; Thikashi Higashino; Tadashi Kozima, both of Yokohama, all of Japan

[73] Assignee: Mitsui Toatsu Chemicals, Inc., Tokyo, Japan

[21] Appl. No.: 240,435

[22] Filed: Mar. 4, 1981

[30] Foreign Application Priority Data

May 27, 1980 [JP] Japan ................................. 55-69591

[51] Int. Cl.$^3$ ............................................. C07C 29/04
[52] U.S. Cl. ................................................... 568/898
[58] Field of Search ............................... 568/898, 901

[56] References Cited

U.S. PATENT DOCUMENTS

| 2,050,445 | 8/1936 | Metzger | 568/898 |
| 2,162,913 | 6/1939 | Eversole et al. | 568/901 |
| 2,798,097 | 7/1957 | Hettinger et al. | 568/901 |
| 3,996,298 | 12/1976 | Izumi et al. | 568/901 |
| 4,060,564 | 11/1977 | Kanemaru et al. | 568/898 |
| 4,236,034 | 11/1980 | Atsushi et al. | 568/901 |

FOREIGN PATENT DOCUMENTS 2024012  1/1980  United Kingdom ............... 568/900

Primary Examiner—Joseph E. Evans
Attorney, Agent, or Firm—Sughrue, Mion, Zinn, Macpeak & Seas

[57] ABSTRACT

Lower alcohols are prepared by hydrating the corresponding olefin in an aqueous solution containing a chromium compound, phosphoric acid and heteropolyacid. Phosphoric acid has a high catalytic activity for the hydration of lower olefins, but causes a remarkable corrosion to an apparatus material under the state of an aqueous solution. The catalytic composition consisting of phosphoric acid and heteropolyacid is improved in activity and stability. Owing to the coexistence of heteropolyacid an acid degree is raised, nevertheless the corrosion of apparatus materials is not increased. As an anti-corrosive a chromium compound is incorporated into the aqueous solution containing the catalytic composition of phosphoric acid and heteropolyacid.

7 Claims, No Drawings

PROCESS FOR PREPARING LOWER ALCOHOLS

BACKGROUND OF THE INVENTION

This invention relates to a process for the preparation of lower alcohols by hydration of the corresponding olefins in a liquid phase.

For the preparation of alcohols by hydration of lower olefins a liquid phase method and a vapor phase method are known and an acidic catalyst is used in their methods. As compared with the vapor phase method the liquid phase method has advantages that alcohols with high conversion can be obtained starting from low-priced olefins of low purity and that utility consumption is small. However, since a strong acidic catalyst is used in the form of an aqueous solution under high temperature and high pressure, there are disadvantages that materials of an apparatus suffer corrosion markedly and the catalyst deteriorates owing to the products of corrosion. By way of example, in the vapor phase method phosphoric acid is used in the form supported on a carrier (U.S. Pat. No. 2,232,610). On the other hand the liquid phase method is disclosed in, for example, Canadian Pat. No. 845,202 and No. 867,797 where phosphoric acid is used in form of an aqueous solution. Under such circumstances that the aqueous solution of phosphoric acid is of high corrosiveness to materials of an apparatus and also, suitable anti-corrosion materials are not yet known, phosphoric acid has not been employed industrially as a catalyst in the liquid phase. According to the processes of the above Canadian patents, a reactor lined with ceramics is used for experiments in a laboratory scale.

Further, as disclosed in, for example, British Pat. No. 1,281,120, heteropolyacids are used as a catalyst in form of an aqueous solution wherein an alkaline substance for adjusting a pH is added to control the corrosion of apparatus materials and accordingly, the catalytic activity is sacrificed therefor.

The inventors found before that chromium compounds dissolved in an aqueous solution of phosphoric acid were effective anti-corrosive in the preparation of lower alcohols by hydration of lower olefins. The processes for effecting the hydration in an aqueous solution of phosphoric acid containing chromium oxyacids or oxyacid salts, or chromium salts and/or chromium complex compounds are disclosed in U.S. Pat. No. 4,060,541 and Japanese Patent Kokai No. 54-19904. These processes are characterized in that the corrosion inhibiting effect is in an elevated temperature with a small amount of anti-corrosive and that chromium compounds are good anti-corrosive even under a strong reducing atmosphere in which olefins and alcohols are present. However, there is a problem of precipitation of the anti-corrosive caused by iron ions which are formed through a slight corrosion and accumulated during the operation. Therefore the corrosion inhibiting effect is reduced and further, the precipitates bring about blocking of reactors and heat exchangers. For solving such problems methods for removing iron ions are proposed, but they result in complicated operation.

SUMMARY OF THE INVENTION

An object of this invention is to provide a catalytic system for the liquid phase method for the preparation of lower alcohols by hydration of lower olefins, enabling to further control corrosion and to maintain a reaction velocity even under lower temperatures.

Another object of this invention is to provide a process for the preparation of lower alcohols by hydration of the corresponding olefins in which the liquid phase method is effectively carried out at lower temperatures and the corrosion of an apparatus material is markedly inhibited.

The foregoing are attained by effecting hydration reaction of lower olefins in an aqueous solution containing a catalytic system consisting of phosphoric acid and heteropolyacid and a chromium compound as an anticorrosive.

DETAILED DESCRIPTION OF THE INVENTION

The heteropolyacids which may be used in this invention are those containing at least one metal atom of molybdenum, tungsten and vanadium. Examples include silicomolybdic acid, phosphomolybdic acid, chromomolybdic acid, nickelmolybdic acid, cobaltmolybdic acid, silicotungstic acid, germanotungstic acid, borotungstic acid, phosphotungstic acid, vanadotungstic acid, cobalttungstic acid, phosphovanadic acid, phosphovanadomolybdic acid, silicocobalttungstic acid, siliconickeltungstic acid, germanocobalttungstic acid, phosphovanadotungstic acid, phosphomolybdotungstic acid and phosphomanganotungstic acid. Among them phosphomolybdic acid, germanotungstic acid, silicotungstic acid, cobalttungstic acid, germanocobalttungstic acid, phosphovanadotungstic acid, borotungstic acid, phosphotungstic acid and silicomolybdic acid are preferred. Particularly preferred are germanotungstic acid, phosphotungstic acid and silicotungstic acid. The heteropolyacid may be used alone or in mixture of two or more.

The concentrations of heteropolyacid and phosphoric acid in an aqueous solution may be both within the range of 0.5–2.0 wt.%, preferably 0.5–1.5 wt.%. In case of the amount of phosphoric acid being less than 0.5 wt.% a good activity for hydration of olefin is not obtained. On the other hand with the amount of more than 2.0 wt.% the corrosion of apparatus materials becomes remarkable and therefore, the catalyst is deteriorated and mechanical losses are increased. Also, with the heteropolyacid concentration of less than 0.5 wt.% a good hydration activity is not obtained, whereas with the concentration of more than 2.0 wt.% the corrosion of apparatus materials becomes remarkable and thus the catalyst is degraded and deteriorated.

In general, it would be foreseen that when other strong acids are added to an aqueous solution of phosphoric acid, an acid degree increases and thus the apparatus material suffers corrosion. On the contrary, in this invention the acid degree is increased by adding heteropolyacids, a strong acid, nevertheless the corrosion is not increased.

Also, owing to the coexistence of phosphoric acid the stability of heteropolyacid is improved. Generally, under a reducing atmosphere such as in the hydration reaction of olefins by the liquid phase method, when heteropolyacids are used in a high concentration at an elevated temperature, they are degraded and decomposed remarkably. However, with the coexistence of phosphoric acid the heteropolyacid is so stabilized that it does not lose the catalytic activity even after repeated use for a long time.

Furthermore, it is said that the catalytic activity of heteropolyacid is remarkably reduced in the presence of a slight amount (10 ppm or more) of iron ions (Japanese Patent Kokai No. 47-31910), nevertheless in the catalytic system of this invention the catalytic activity of heteropolyacids is not reduced even in the presence of iron ions of 100 ppm and sufficient reaction velocity can be maintained.

The corrosion inhibiting effect is markedly improved by dissolving a chromium compound in the phosphoric acid solution. This corrosion inhibiting mechanism is not made clear, though it is considered that the chromium compound dissolved is bonded with phosphoric anions, hydrogen phosphoric anions and heteropolyacid anions around chromium ions (III) as a central atom thereby forming aquocomplex which acts on the wall of apparatus to exhibit the anti-corrosive effect.

The chromium compounds which may be used in this invention are those which are soluble in the aqueous solution of phosphoric acid and heteropolyacid, for example, chromium salts such as chromium phosphate, chromium nitrate, chromium carbonate, chromium oxalate and chromium sulfate; chromic acid, chromate and bichromate, such as sodium chromate, potassium chromate, chromic anhydride, sodium bichromate and potassium bichromate; chromium complex compounds such as tetraaquodiaminechromium sulfate and tripotassium hexaaminochromate; chromium hydroxide. Preferred are chromium phosphate, chromium hydroxide, chromium anhydride, sodium chromate and potassium chromate.

The chromium compound may be added direct to the aqueous solution of phosphoric acid and heteropolyacid as the catalyst solution. Alternatively, the chromium compound may be added to an aqueous solution in high concentration of phosphoric acid or a mixture of phosphoric acid and heteropolyacid and heated to dissolve completely, followed by diluting to desired concentrations of the catalyst solution. Further, after addition of the chromium compound to the catalyst solution, lower alcohols are added and heated to dissolve the chromium compound which is then reduced to trivalent chromium in case of being hexavalent chromium. The amount of the chromium compound used may be within the range of preferably 0.0001–0.1 wt.% as chromium atom. When the amount exceeds 0.1 wt.%, the anti-corrosive effect is not particularly improved. More preferred is the range of 0.0001–0.05 wt.%.

The catalytic system according to this invention has a very high hydration activity so that the hydration of olefins by the liquid phase method can be carried out at a comparatively low temperature whereby alcohols can be prepared conveniently in point of view of chemical equilibrium. By way of example, the preparation of isopropyl alcohol by hydration of propylene in the liquid phase method has been carried out in a commercial scale at temperatures of 240°–270° C. ("Catalyst" vol. 18, No. 6, pp 180-184, 1976). However, according to this invention the hydration reaction is advanced with high velocity at a relatively low temperature of 200°–240° C. Therefore the hydration of propylene is carried out conveniently in point of view of chemical equilibrium, the corrosion of apparatus materials is reduced and further, a side reaction such as polymerization of propylene is inhibited.

Also, according to this invention the corrosion of apparatus material is reduced markedly so that the formation and accumulation of iron ions during the operation is decreased and therefore, precipitates of the anticorrosive owing to the iron ion become less. Accordingly, the corrosion inhibiting effect is further improved and the blocking of apparatus owing to the precipitates is overcome.

In case the hydration reaction in the aqueous solution containing the chromium compound, phosphoric acid and heteropolyacid is accompanied with a side reaction such as polymerization of olefins and thus, selectivity to alcohols is reduced, it is possible to adjust a pH of the aqueous solution in the range of 1.4–2.4 thereby inhibiting the side reaction and maintaining the consumption of olefin favourably. When the pH is less than 1.4 polymerization of olefins takes place. On the other hand, when the pH exceeds 2.4, a sufficient reaction velocity can not be maintained.

For retaining the pH of the aqueous solution in the suitable range as above, water-soluble basic compounds, for example metal hydroxides or metal oxides, such as NaOH, $Al(OH)_3$, $Mg(OH)_2$, $Zn(OH)_2$, MgO and ZnO may be added. Besides these compounds those which are water-soluble and can retain the pH in the range of 1.4–2.4 may be also used. Further, water-soluble salts of phosphoric acid and/or heteropolyacid may be dissolved in the aqueous solution containing phosphoric acid and heteropolyacid to adjust the pH in the range of 1.4–2.4.

Lower olefins which may be used in this invention are, for example, ethylene, propylene, n-butene, isobutene, pentene and hexene. Alcohols used herein mean ones obtained by the hydration reaction of the above olefins. The process of this invention is, particularly, effective for the preparation of isopropyl alcohol by hydration of propylene.

While contacting the lower olefin with the aqueous solution prepared as above, the corresponding alcohol can be easily produced in known hydration reaction apparatus of batch type or continuous type. The reaction temperature is, preferably, within the range of 100°–300° C., though it may be selected suitably depending on the kind of olefins. By way of example, preferred is 240°–280° C. for ethylene, 200°–240° C. for propylene and 150°–240° C. for butene. The reaction pressure may be more than a saturated vapour pressure under which the aqueous solution of catalyst is present in form of liquid at applied temperature, though high pressure of usually, 100–300 kg/cm$^2$G is preferred for obtaining a high reaction velocity.

For carrying out the reaction effectively, the aqueous solution of catalyst and olefins are brought into contact in parallel current or counter current by means of a general absorption tower and then, unreacted olefins are separated from the reaction product solution coming from the tower, followed by separating alcohols through distillation and extraction. The aqueous solution of catalyst is recovered and recycled to the reaction tower where it can be used repeatedly without separating the catalyst.

The apparatus materials normally used in the process of this invention may be a stainless steel for general use, though a stainless steel containing 20–30 wt.% of chromium and 10–25 wt.% of nickel is particularly preferred. Also, preferred is a stainless steel containing ingredients improving an anti-corrosiveness such as molybdenum, tantalum and niobium.

Since this invention has many characteristics as mentioned above, in the industrial practice alcohols can be produced effectively and conveniently from the economical point of view. By way of example, this invention has the following advantages:
(1) The preparation of alcohols by contacting the aqueous solution of catalyst with olefins can be carried out at a relatively low temperature so that the alcohol concentration in the reaction solution is raised in equilibrium. Accordingly, the recycling amount of the aqueous catalyst solution is reduced and thus, the utility consumption for electric power and steam can be markedly saved.
(2) Owing to a low temperature condition and effects of anti-corrosive, the corrosion of apparatus materials is extremely reduced so that the maintenance of apparatus is easy.
(3) Heteropolyacids are stabilized by addition of phosphoric acid and therefore, there is little deterioration or loss of the catalyst.
(4) Since a low-priced stainless steel can be used as apparatus material, there are economical advantages that the cost of construction falls.

This invention will be illustrated by the following non-limitative examples.

A corrosion rate used herein is determined by the following formula:

Corrosion rate (mm/year) = Amount of corrosion of test pieces (g) × Hours of a year (hr) × 10/Surface area of test pieces (cm$^2$) × Hours for test (hr) × Density of test pieces (g/cm$^3$)

EXAMPLE 1

Test pieces of SUS-304 and SUS-316 were fitted out to a stirring rod of a zirconium autoclave of 300 ml in capacity in the state of both being insulated from each other. An aqueous solution containing 10 ppm of chromium phosphate (as chromium atom), 1.0 wt.% of phosphoric acid and 1.0 wt.% of germanotungstic acid and propylene were continuously fed at velocity of 300 ml/hr and 90 g/hr, respectively into the autoclave and heated while stirring vigorously. Temperature was elevated to 230° C. and pressure to 200 kg/cm$^2$G, and reaction was carried out for 240 hours while separating unreacted propylene from the reaction product solution.

After completion of the reaction the test pieces were taken out from the autoclave and corrosion rates on SUS-304 and SUS-316 were measured and were 0.015 mm/year and 0.010 mm/year, respectively.

At this time, the solution drawn out from the autoclave was subjected to gas chromatography and as a result, the concentration of isopropyl alcohol was 12.9 wt.% and isopropyl ether and acetone were formed in small amounts. Also, chromium atom in the drawn solution was analyzed to be 10 ppm and therefore, chromium phosphate was not consumed.

EXAMPLE 2

To an aqueous solution having a 1.0 wt.% concentration of phosphoric acid were added 20 ppm of an anti-corrosive (as chromium atom) and heteropolyacid and a pH was adjusted as indicated in Table 1.

Corrosion tests were effected in the same procedure as in Example 1. For comparison the above test was repeated except not adding heteropolyacids and an anti-corrosive. The results obtained are set forth in Table 1.

TABLE 1

| Run No. | Olefins | Heteropolyacids Type | Conc. wt. % | H$_3$PO$_4$ Conc. wt. % | Anti-corrosives | pH | Temp. °C. | Press. kg/cm$^2$G | Time hr | Material | Corrosion rate mm/year |
|---|---|---|---|---|---|---|---|---|---|---|---|
| 1 | Propylene | None | — | 1.0 | None | 1.63 | 230 | 200 | 144 | SUS-310S | 0.78 |
| 2 | " | None | — | " | None | " | " | " | " | SUS-316L | 1.38 |
| 3 | " | Borotungstic acid | 1.0 | " | Chromium hydroxide | 1.53 | " | " | 168 | " | 0.015 |
| 4 | " | Silicotungstic acid | " | " | Chromium hydroxide | 1.52 | 200 | " | " | " | 0.017 |
| 5 | " | Cobalttungstic acid | " | " | Chromium nitrate | 1.54 | 230 | " | " | " | 0.012 |
| 6 | " | Phosphotungstic acid | " | " | Chromium phosphate | 1.48 | " | " | " | SUS-304 | 0.034 |
| 7 | " | Phosphomolybdic acid | " | " | Chromium phospate | 1.45 | " | " | 120 | SUS-310S | 0.010 |
| 8 | " | Phosphotungstic acid | " | 2.0 | Chromium phosphate | 1.50* | " | " | 168 | SUS-316 | 0.030 |
| 9 | " | Silicotungstic acid | " | 1.0 | Sodium chromate | 1.54 | " | " | 120 | " | 0.010 |
| 10 | Ethylene | Phosphotungstic acid | " | " | Chromium phosphate | 1.50 | 270 | " | " | SUS-310S | 0.086 |

*Adjusted by addition of NaOH

EXAMPLE 3

An aqueous solution was prepared by adding 10 ppm of an anti-corrosive (as chromium atom), phosphoric acid and heteropolyacid in concentration ranges as recited in this invention. 300 ml of the aqueous solution obtained were fed into a tantalum autoclave of 500 ml in capacity and heated while stirring vigorously. Olefin was fed at indicated temperatures and while carrying out a hydration reaction, stability of heteropolyacids were tested for indicated time.

After the test, the heteropolyacid in the reaction product solution was subjected to polarographic analysis to measure its decomposition rate. The results are set forth in Table 2. For comparison the results on examples not adding phosphoric acid and an anti-corrosive are also set forth.

TABLE 2

| Run No. | Olefin | Heteropolyacids Type | Conc. wt. % | H$_3$PO$_4$ Conc. wt. % | Anti-corrosive | pH | Temp. °C. | Press. kg/cm$^2$G | Time hr | Alcohol Conc. wt. % | Heteropolyacid Decomposition rate, % |
|---|---|---|---|---|---|---|---|---|---|---|---|
| 1 | Propylene | Germanotungstic | 1.0 | None | None | 2.0 | 250 | 200 | 125 | 8.6 | 4.6 |

TABLE 2-continued

| Run No. | Olefin | Heteropolyacids Type | Conc. wt. % | H₃PO₄ Conc. wt. % | Anti-corrosive | pH | Temp. °C. | Press. kg/cm²G | Time hr | Alcohol Conc. wt. % | Heteropolyacid Decomposition rate, % |
|---|---|---|---|---|---|---|---|---|---|---|---|
| 2 | " | Phosphotungstic acid | " | " | " | 2.0 | 250 | " | 135 | 8.5 | 4.9 |
| 3 | " | Silicotungstic acid | " | " | " | " | " | " | " | 8.6 | 5.9 |
| 4 | " | Phosphomolybdic acid | " | " | " | " | 240 | " | " | 8.5 | 6.1 |
| 5 | " | Germanotungstic acid | " | 1.0 | Chromium phosphate | 1.55 | 250 | " | 340 | 8.5 | 0.41 |
| 6 | " | Phosphotungstic acid | " | " | Chromium phosphate | " | " | " | 155 | 8.4 | 0.20 |
| 7 | " | Silicotungstic acid | " | " | Chromium phoshpate | " | " | " | 120 | 8.5 | 0.31 |
| 8 | " | Phosphomolybdic acid | " | " | Chromium phosphate | 1.50 | 230 | " | " | 11.0 | 0.76 |
| 9* | " | Germanotungstic acid | " | " | Chromium phosphate | 1.56 | 250 | " | 135 | 8.5 | 0.17 |
| 10* | " | Phosphotungstic acid | " | " | Chromium phosphate | 1.56 | " | " | " | 8.5 | 0.18 |

*Iron phosphate (III) was added until the concentration of iron ion in the aqueous solution had reached 100 ppm.

EXAMPLE 4

To a 1.0 wt.% aqueous solution of phosphoric acid containing 20 ppm of an anti-corrosive (as chromium atom) was heteropolyacid added in such a manner that its concentration became 1.0 wt.%. Using the aqueous solution of catalyst obtained, a hydration reaction of lower olefins was carried out in the same procedure as in Example 1. The results are set forth in Table 3.

and then, propylene gas was fed. While effecting a hydration reaction, pressure was adjusted to 200 kg/cm²G. A corrosion test was carried out at 230° C. under 200 kg/cm²G for 120 hours and as a result, the isopropyl alcohol concentration in the reaction product solution was 13.0 wt.% and corrosion rates of SUS-304, SUS-316 and SUS-310S were 0.90 mm/year, 0.75 mm/year and 0.35 mm/year, respectively.

For comparison the corrosion test was carried out

TABLE 3

| Run No. | Olefin | Heteropolyacid Type | Conc. wt. % | H₃PO₄ Conc. wt. % | Anti-corrosive | pH | Temp. °C. | Press. kg/cm²G | Time hr | Alcohol Conc. wt. % | Selectivity to % |
|---|---|---|---|---|---|---|---|---|---|---|---|
| 1 | Ethylene | Germanotungstic acid | 1.0 | 1.0 | Chromium phosphate | 1.55 | 280 | 250 | 1.0 | 6.0 | 99 |
| 2 | Propylene | Germanotungstic acid | " | " | Chromium phosphate | " | 230 | 200 | 0.5 | 14.0 | 98 |
| 3 | " | Phosphotungstic acid | " | " | Chromium hydroxide | " | " | " | " | 13.5 | 98 |
| 4 | " | Silicotungstic acid | " | " | Chromium hydroxide | " | " | " | " | 13.6 | 98 |
| 5 | " | Phosphomolybdic acid | " | " | Chromium hydroxide | 1.50 | " | " | 0.4 | 13.5 | 98 |
| 6 | Iso-butylene | Germanotungstic acid | " | " | Chromium phosphate | 1.55 | 150 | 40 | 1.0 | 16.0 | 98 |
| 7 | Propylene | Germanotungstic acid | 0.3 | 0.3 | Chromium phosphate | 2.60 | 230 | 200 | 0.5 | 4.0 | 100 |
| 8 | " | Germanotungstic acid | 2.5 | 2.5 | Chromium phosphate | 1.20 | " | " | " | 8.0* | 92 |

*Isopropyl ether and oligomers were formed in large quantities.

REFERENCE EXAMPLE 1

To a 1.0 wt.% aqueous solution of phosphoric acid was phosphovanadotungstic acid {H₇[P(W₂O₇)₃.(V₂O₆)₃].30 H₂O} added in such a manner that its concentration became 0.5 wt.%. The aqueous solution of catalyst thus obtained had a pH of 1.59.

On the other hand, test pieces for corrosion test were fitted out to a stirring rod of a tantalum autoclave of 500 ml in capacity in such a manner that they were insulated from one another by Teflon sheet (the tradename by Du Pont). Then, 300 ml of the above aqueous solution were fed into the autoclave, the inside of which was purged by nitrogen gas and filled therewith. Heating was rapidly effected to temperature of 230° C. under stirring under the above conditions without adding phosphovanadotungstic acid for 100 hours. At this time a pH was 1.65. The corrosion rates of SUS-304, SUS-316 and SUS-310S were 1.75 mm/year, 1.37 mm/year and 0.78 mm/year, respectively.

As is apparent from the foregoing, with addition of phosphovanadotungstic acid to the aqueous solution of phosphoric acid, the acid degree increases to a pH of 1.59 from a pH of 1.65, nevertheless the corrosion of the materials is reduced.

REFERENCE EXAMPLE 2

The test of Reference Example 1 was repeated except using phosphoric acid and heteropolyacids as indicated in Table 4.

TABLE 4

| Run No. | Heteropolyacids Type | Conc. wt. % | H$_3$PO$_4$ Conc. wt. % | pH | Temp. °C. | Press. kg/cm$^2$G | Time hr | Material | Corrosion rate mm/year |
|---|---|---|---|---|---|---|---|---|---|
| 1 | Germanotungstic acid | 1.0 | 1.0 | 1.50 | 240 | 200 | 240 | SUS-310S | 0.40 |
| 2 | Phosphotungstic acid | " | " | 1.49 | " | " | 192 | SUS-310S | 0.56 |
| 3 | Phosphomolybdic acid | " | " | 1.50 | " | " | " | SUS-310S | 0.45 |
| 4 | None | — | " | 1.65 | " | " | " | SUS-310S | 0.60 |

What is claimed is:

1. A process for the preparation of lower alcohols by hydration of the corresponding olefins in an aqueous solution, which comprises effecting the hydration reaction in an aqueous solution containing a catalytic system consisting of 0.5 to 2 wt.% of phosphoric acid and 0.5 to 2 wt.% of a heteropolyacid and a chromium compound as an anti-corrosive, the aqueous solution having a pH of 1.4 to 2.4 and reaction being conducted at a temperature of 100° to 300° C.

2. The process of claim 1 wherein said chromium compound is one which is soluble in the aqueous solution of phosphoric acid and heteropolyacid.

3. The process of claim 1 wherein said heteropolyacid is one containing at least one metal atom of molybdenum, tungsten and vanadium.

4. The process of claim 1 wherein said heteropolyacid is at least one member selected from the group of germanotungstic acid, silicotungstic acid, phosphotungstic acid, borotungstic acid, phosphomolybdic acid, silicomolybdic acid, cobalttungstic acid, germanocobalttungstic acid and phosphovanadotungstic acid.

5. The process of claim 1 wherein the concentration of chromium compound in the aqueous solution is within the range of 0.0001–0.1 wt.% as chromium atom.

6. The process of claim 1, wherein from 0.5 to 1.5 wt.% of said heteropolyacid is present.

7. The process of claim 1, wherein the concentration of chromium compound in the aqueous solution is within the range of 0.0001 to 0.05 wt.% as chromium atom.

* * * * *